United States Patent
Subramanian et al.

(10) Patent No.: US 6,819,427 B1
(45) Date of Patent: Nov. 16, 2004

(54) APPARATUS OF MONITORING AND OPTIMIZING THE DEVELOPMENT OF A PHOTORESIST MATERIAL

(75) Inventors: Ramkumar Subramanian, San Jose, CA (US); Michael K. Templeton, Atherton, CA (US); Bharath Rangarajan, Santa Clara, CA (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 418 days.

(21) Appl. No.: 09/973,849

(22) Filed: Oct. 10, 2001

(51) Int. Cl.[7] .................. G01N 21/55; G01N 21/00
(52) U.S. Cl. ..................... 356/445; 356/237.1
(58) Field of Search .................. 356/445–448, 356/237.1, 237.2; 118/52–54, 712, 600, 667, 107, 218, 232, 233, 319; 427/8, 9, 240

(56) References Cited

U.S. PATENT DOCUMENTS

| | | | |
|---|---|---|---|
| 4,025,344 A | * 5/1977 | Allen et al. .................... 96/50 |
| 4,136,940 A | * 1/1979 | Lin .............................. 354/298 |
| 4,618,564 A | 10/1986 | Demmer et al. ............ 430/270 |
| 5,208,133 A | 5/1993 | Tsumori ....................... 430/270 |
| 5,213,946 A | 5/1993 | Shirai et al. ................. 430/270 |
| 5,607,800 A | * 3/1997 | Ziger ............................. 430/8 |
| 5,885,745 A | 3/1999 | Marrocco, III ........... 430/270.1 |
| 5,998,092 A | 12/1999 | McCulloch et al. ...... 430/270.1 |
| 6,248,175 B1 | * 6/2001 | Subramanian et al. ...... 118/712 |
| 6,327,035 B1 | * 12/2001 | Li et al. ...................... 356/432 |
| 6,376,013 B1 | * 4/2002 | Rangarajan et al. ........ 427/240 |
| 6,383,824 B1 | * 5/2002 | Lensing ....................... 438/14 |
| 6,541,184 B1 | * 4/2003 | Subramanian et al. ...... 430/311 |
| 6,549,287 B1 | * 4/2003 | Lensing et al. ............. 356/601 |

* cited by examiner

*Primary Examiner*—Michael P. Stafira
(74) *Attorney, Agent, or Firm*—Amin & Turocy, LLP

(57) ABSTRACT

A system and method is provided that facilitates the uniform development of a pattern on a photoresist material layer using a developer. The present invention accomplishes this end by considering the acid-base relationship of the photoresist material and developer and monitoring the development of water formed in the development process. Typically, photoresist material is purchased or manufactured with known concentrations of resin and photoacid generator. Therefore, by monitoring the development of water in the development process, the present invention can measure the acid consumption in the development process. The present invention can then utilize this information in optimizing the developer volume, developer concentration and developer time to improve the quality of the developed image pattern on the photoresist material layer.

23 Claims, 9 Drawing Sheets

US 6,819,427 B1

APPARATUS OF MONITORING AND OPTIMIZING THE DEVELOPMENT OF A PHOTORESIST MATERIAL

TECHNICAL FIELD

The present invention generally relates to semiconductor processing, and in particular to a system for optimal development of a photoresist material layer on a wafer.

BACKGROUND OF THE INVENTION

In the semiconductor industry, there is a continuing trend toward higher device densities. To achieve these high densities there has been and continues to be efforts toward scaling down device dimensions (e.g., at submicron levels) on semiconductor wafers. In order to accomplish such high device packing density, smaller and smaller features sizes are required. This may include the width and spacing of interconnecting lines, spacing and diameter of contact holes, and the surface geometry such as corners and edges of various features.

The requirement of small features with close spacing between adjacent features requires high resolution photolithographic processes. In general, lithography refers to processes for pattern transfer between various media. It is a technique used for integrated circuit fabrication in which a silicon structure or wafer is coated uniformly with a radiation-sensitive film, the resist, and an exposing source (such as optical light, x-rays, or an electron beam) illuminates selected areas of the surface through an intervening master template, the mask, for a particular pattern. The lithographic coating or resist is generally a radiation-sensitive coating suitable for receiving a projected image of the subject pattern.

The resist can be classified into a positive type resist or a negative type resist based on the type of reaction, and a two component or a three component type based on the number of components in the resist. A positive type resist becomes more soluble in an aqueous based developer when exposed to radiation and negative type resist becomes less soluble in an aqueous based developer when exposed to radiation. A two component type includes a base resin, such as a photosensistive organic compound and a photoacid generator. A photoacid generator is a compound that is neutral, but which decomposes to form an acid upon exposure to light energy at particular wavelengths or frequencies. The photosensitive organic compound is a compound that absorbs light at different wavelengths and thereafter transfers energy to the photoacid generator to form the acid. A three component type includes a base resin, a photoacid generator and an acid-crosslinking agent. Exposure of the resist through a photomask causes the image area to become either more or less soluble (depending on the coating) in a particular solvent developer. The solvent is a base and the more soluble areas of the resist are removed in the developing process to leave the pattern image in the coating. The patterned image is used as a mask for etching the pattern into the wafer. The resist is then stripped from the wafer leaving the patterned image etched into the wafer.

Application of the resist onto the wafer is typically accomplished by using a spin coater. The spin coater is essentially a vacuum chuck rotated by a motor. The wafer is vacuum held onto the spin chuck. Typically, a nozzle supplies a predetermined amount of resist to a center area of the wafer. The wafer is then accelerated to and rotated at a certain speed, and centrifugal forces exerted on the resist cause the resist to disperse over the whole surface of the wafer. After the resist is spin coated and selectively irradiated to define a predetermined pattern, the irradiated or nonirradiated portions are removed by applying a developer. The developer is also spin coated onto the wafer by applying developer across the resist and then spin coating the developer until centrifugal forces disperse the developer over the coating of resist. After a predetermined time, the photoresist material layer becomes developed and the irradiated or nonirradiated portions are removed by rinsing or washing with a washing solution material.

However, the rate of development may vary based on the amount and concentration of the photoacid generator in the resist, the identity of the photoacid generated, the identity of the developer, the concentration and volume of the developer and the amount of time that the resist is exposed to the developer. Failure to use the appropriate amount/concentration of developer and/or appropriate exposure time for a given photoacid generator and developer results in nonuniform quality of the imaged pattern across the resist and ultimately wafer defects.

In view of the above, a system/method is needed, for dispensing an optimal volume and concentration of developer across a photoresist material layer formed on a wafer for an optimal period of development time.

SUMMARY OF THE INVENTION

The present invention provides for a system and method that facilitates the uniform development of a pattern on a photoresist material layer using a developer. The present invention accomplishes this end by considering the acid-base relationship of the photoresist material and developer and monitoring the development of water formed in the development process. Typically, photoresist material is purchased or manufactured with known concentrations of resin and photoacid generator. Therefore, by monitoring the development of acid or formation of water in the development process, the present invention can measure the acid consumption in the development process. The present invention can then utilize this information in optimizing the developer volume, developer concentration and development time to improve the quality of the developed image pattern on the photoresist material layer.

A developer plate can be employed forming a parallel plate pair with the wafer during application of the developer. The developer plate is disposed in very close proximity with respect to the wafer, such that the developer is squeezed between the two plates thereby spreading evenly the developer over the wafer. Since the developer film is stagnant, the transport of acid into base can be monitored and therefore, the development process can be monitored. Furthermore, the proximity of the developer plate to the wafer during application and the size of a plurality of apertures in the developer plate provides for improved localization with respect to development of the photoresist material layer.

In one aspect of the invention, a monitoring or measurement system is provided that measures the amount of water formed in a development process of a photoresist material. The measuring can be accomplished utilizing various techniques. For example, the measuring may be conducted on a test or reference wafer off-line utilizing conventional lab measuring techniques. Using the measured results, adjustments can be made to the developer volume, developer concentration and/or development time until an optimal result is achieved. The measuring may be accomplished by employing in situ laser scattering or laser doppler anemometry techniques. Additionally, the measuring may be accomplished by employing light scattering techniques, such as interferometry and spectrometry. The laser scattering and light scattering techniques can be employed in providing a close loop system, such as a control system for continuously improving the acid consumption of the development process.

One particular aspect of the invention relates to a method of developing a selectively irradiated photoresist material layer disposed on a semiconductor wafer. The method includes contacting the photoresist material layer with a volume of developer having a concentration for a period of time whereby the developer and an acid in the photoresist material layer interact to generate an amount of water, measuring the amount of water, determining an amount of acid consumption based on the amount of water measured and adjusting at least one of the developer volume, concentration and contact time based on the amount of acid consumption determined.

Another aspect of the invention relates to a system for monitoring development of a selectively irradiated photoresist material layer. The system includes at least one light source disposed near the selectively irradiated photoresist material layer where the at least one light source is adapted to transmit a ray of light across the selectively irradiated photoresist material layer. The system also includes at least one detector disposed near the selectively irradiated photoresist material layer where the at least one detector is adapted to receive a reflected ray of light due to the at least one light source and provide a signal corresponding to the intensity of the reflected ray of light. The system further includes a measuring system operably coupled to the at least one detector where the measuring system is adapted to receive the signal corresponding to the intensity of the ray of light and convert the signal to digital data. A processor is operatively coupled to the measuring system. The processor is adapted to receive the digital data from the measuring system and analyze the digital data wherein the difference of the intensity of the ray of light from the at least one light source to when it is received by at least one detector is proportional to an amount of water generated across the selectively irradiated photoresist material layer due to an interaction of a developer and an acid in the selectively irradiated photoresist material layer.

In yet another aspect of the invention, a system of controlling development of a selectively irradiated photoresist material layer is provided. The system includes a nozzle adapted to contact the selectively irradiated photoresist material layer with a volume of developer having a concentration for a period of time, a measuring system adapted to measure an amount of water generated on the selectively irradiated photoresist material layer due to an interaction of the developer and an acid in the selectively irradiated photoresist material layer and a processor operatively coupled to the measuring system and a developer volume and concentration control system. The processor receives data from the measuring system relating to the amount of water measured and the processor uses the data to determine an amount of acid consumption of the selectively irradiated photoresist material layer. The processor is further adapted to provide adjustment information to the developer volume and concentration control system for adjusting at least one of a developer volume, a developer concentration and a developer contact time, so that a subsequent selectively irradiated photoresist material layer having a more uniform development can be achieved.

In another aspect of the invention, a system of developing a selectively irradiated photoresist material layer disposed on a semiconductor wafer is provided.

The system includes means for applying a developer to the selectively irradiated photoresist material layer, means for measuring an amount of water generated on the selectively irradiated photoresist material layer due to an interaction of the developer and an acid in the selectively irradiated photoresist material layer and means for determining an amount of acid consumption of the selectively irradiated photoresist material layer based on the amount of water measured.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other advantages and novel features of the invention will become apparent from the following detailed description of the invention when considered in conjunction with the drawings.

DETAILED DESCRIPTION OF THE INVENTION

Figure 1A:
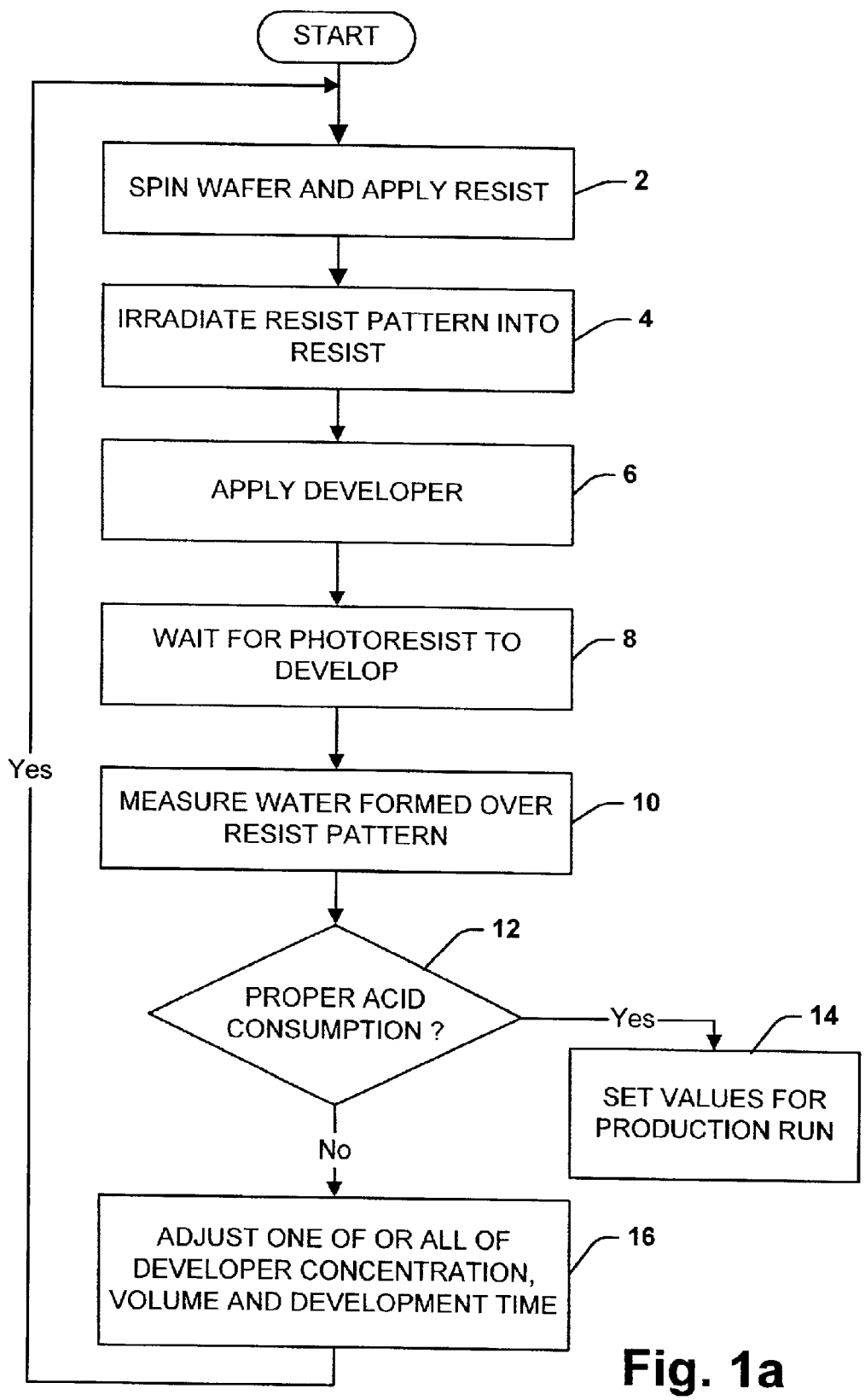
FIG. 1a is a flow diagram illustrating one specific methodology for carrying out the present invention.

The present invention refers to a model for improving the development process of a patterned photoresist material layer disposed on a semiconductor wafer. The model takes into consideration known characteristics of photoacid generators in the photoresist material layer (e.g., concentration, composition, volume ratio, etc.) and known characteristics of a developer used in conjunction with the development of the photoresist material (e.g., concentration, volume, chemical reaction ratio, etc.) to optimize the development of a patterned image onto the photoresist material. The model accomplishes this end by evaluating the water formed across the patterned image as a result of the acid-base reaction during the development process and adjusts at least one of the developer volume, developer concentration and development time to optimize the development process.

The present invention will now be described with reference to the drawings, wherein like reference numerals are used to refer to like elements throughout. The present invention will be described with reference to a method of measuring water present in a development process of a photoresist material and adjustment of the volume, concentration and development time of a developer used in the process. In addition, the present invention will be described with reference to a system and method for monitoring and controlling the developer volume, developer concentration and development time of a developer applied onto a photoresist material layer in order to form a uniformly developed patterned photoresist. It is to be understood that the description of these embodiments are merely illustrative and that they should not be taken in a limiting sense.

FIG. 1a is a flow diagram illustrating one particular methodology for carrying out the present invention. In step 2, a test wafer is placed on a spin chuck and a photoresist material layer is spin rotated onto the wafer. In step 4, a pattern is irradiated onto the resist. In step 6, a developer of a certain concentration and volume is applied onto the wafer and the photoresist material is developed after a development time in step 8. The developer can be spin coated onto the photoresist material layer. In step 10, the amount of water formed over the resist caused by the acid-base properties of the photoresist and developer is determined using conventional techniques, such as laboratory measurement equipment or the like, while the test wafer rests on the chuck or after the test wafer is removed from the chuck. The developer and the irradiated or unirradiated resist portions can then be rinsed off the photoresist material layer using a washing solution or the like. In step 12, the amount of acid consumption is determined based on the amount of water measured in the development process and it is determined if the proper amount of acid consumption has occurred. If the proper amount of acid consumption has occurred (Yes), the values of the developer concentration, the developer volume and the development time are set for production in step 14. If the proper amount of acid consumption has not occurred (No), one or all of the developer concentration, the developer volume and the development time are adjusted and the method returns to step 2 for repeating the above steps for another wafer.

Figure 1B:
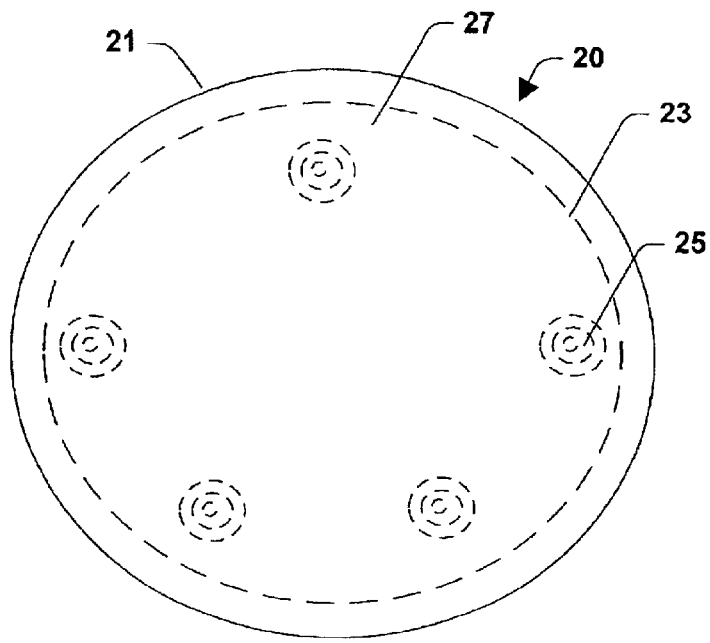
FIG. 1b is a bottom view of a developer application system in accordance with one particular aspect of the present invention.
Figure 1C:
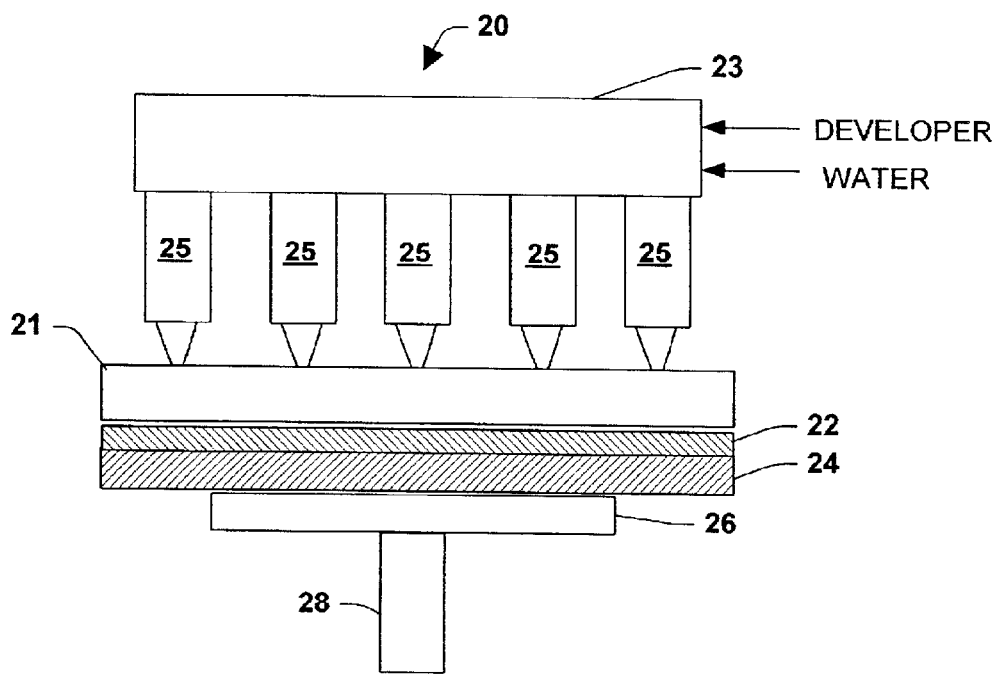
FIG. 1c is a front view of the developer application system of FIG. 1b during application of developer on a wafer in accordance with one particular aspect of the present invention.

FIGS. 1b and 1c illustrate a development application system 20. The development application system 20 includes a developer supply system 23, a plurality of nozzle assemblies 25 and a parallel developer plate 21. The parallel developer plate 21 includes a plurality of apertures 27 extending therethrough for applying a developer to a photoresist material 22 that has been spin coated onto a wafer 24. The wafer 24 is vacuum held onto a rotating chuck 26. The wafer 24 is spin rotated by a shaft 28 driven by a motor (not shown), so that a photoresist material can be applied to the wafer 24 to form a uniform film or layer of photoresist material 22 over the wafer 24. After the photoresist material is dried, suitable photolithographic techniques (e.g. irradiation, development) may be performed to form a patterned photoresist material layer.

The developer plate 21 forms a parallel plate pair with the wafer 24 during application of the developer. The developer supply system 23 is provided with a supply of concentrated developer (not shown) and a supply of water (not shown) for allowing variation of the concentration of the developer. The nozzles provide the developer plate 21 with a volume of developer for application to the patterned photoresist material layer 22. The developer plate 21 is disposed in very close proximity with respect to the wafer 24, such that the developer is squeezed between the two plates (i.e., the developer plate 21 and the wafer 24) thereby spreading evenly the developer over the wafer. Since the developer film is stagnant, the transport of acid into base can be monitored and therefore, the development process can be monitored. Furthermore, the proximity of the developer plate 21 to the wafer 24 during application and the size of the plurality of apertures provides for improved localization with respect to development of the photoresist material layer 22.

Figure 2A:
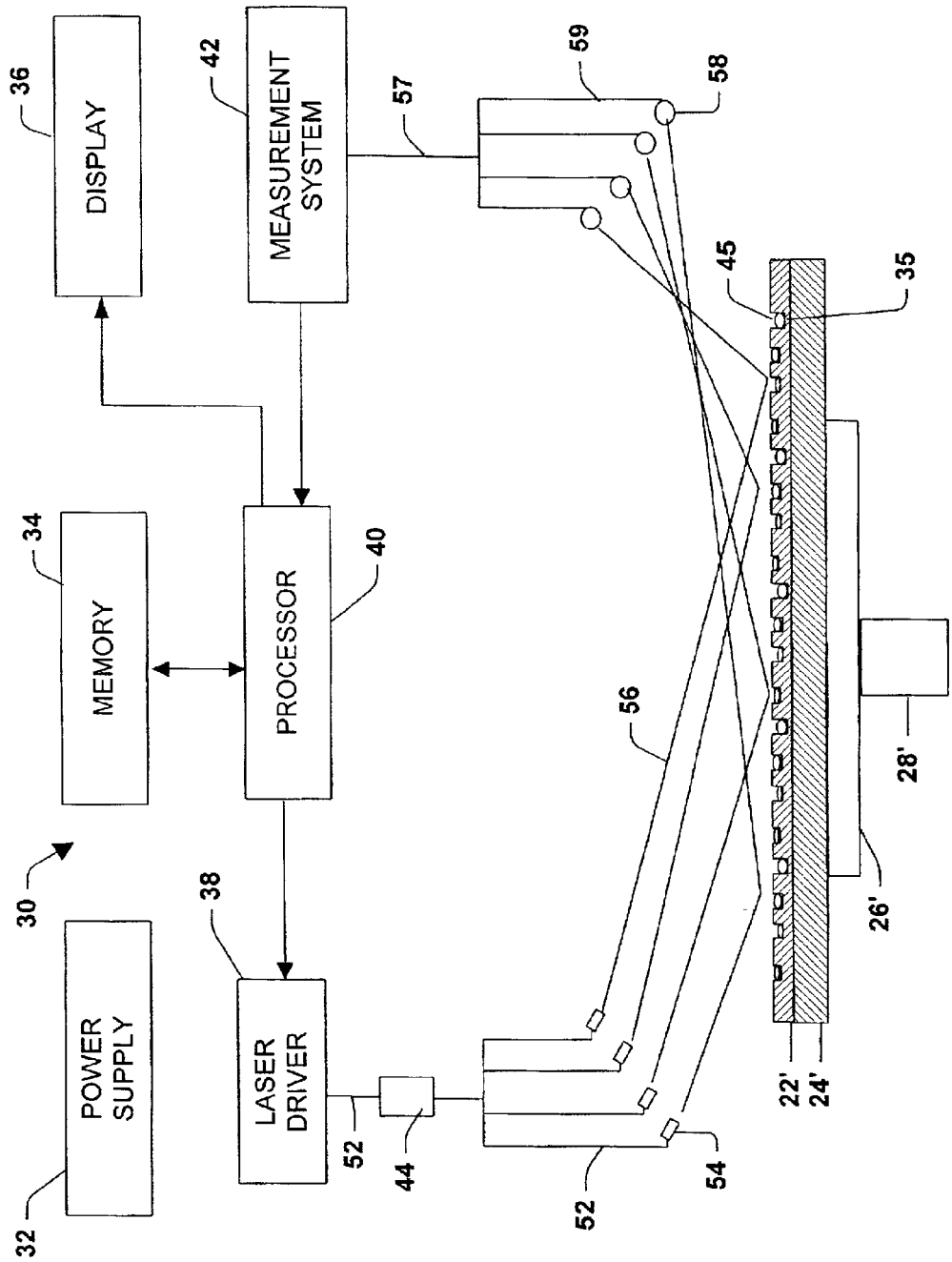
FIG. 2a is a representative schematic block diagram of a monitoring system in accordance with one particular aspect of the present invention.

Referring to FIG. 2a, a system 30 for monitoring the amount of acid consumption in a development process of a patterned photoresist layer is illustrated A nozzle (not shown) applies a photoresist material to the center of a wafer 24' that is vacuum held onto a rotating chuck 26'. The wafer 24' is spin rotated by a shaft 28' driven by a motor (not shown), so that the photoresist material forms a uniform film or layer over the wafer 24'. After the photoresist material is dried, suitable photolithographic techniques (e.g. irradiation, development) may be performed to form a patterned photoresist material layer 22' in a desired manner. The system 30 further includes a water particle measurement system 42. A plurality of lasers 54 are connected to a laser source 44 by fiber optic lines 52. The laser source 44 is coupled to a laser driver 38 also by fiber optic lines 52. The laser driver 44 is turned on and off for water particle count measurements by a processor 40. The patterned photoresist material layer 22' includes a plurality of vias 35 containing water particles 45 therein as a result of the acid-base characteristics of the photoresist material and the developer after a development process is performed.

The plurality of lasers 54 send rays of light 56 onto the patterned photoresist material layer 22'. The rays of light 56 are reflected to a plurality of detectors 58 which are coupled to the measurement system 42 for measuring the water particle count on the patterned photoresist material layer 22'. The light 56 will have different reflecting characteristics if interrupted by water particles 45 as opposed to the patterned photoresist material layer 22' and the vias 45, thus varying the intensity of the light 56 received by the detectors 58. Each laser 54 has a corresponding detector 58 for measuring water particle counts. Each laser and detector pair are positioned to detect water particles at different areas within the patterned photoresist material layer. The detectors 58 are connected to the measurement system 42 by fiber optic lines 57 and provide the processor 40 with water particle count information. The processor 40 analyzes the water particle count information, after it is converted into digital form by the measurement system 42. The processor 40 then outputs the water particle count to a display 36 in a format understandable to a user.

It is to be appreciated that lasers 54 and the detectors 58 may be rotatable with respect to the photoresist material layer 22', so that water particle count measurements can be performed at various points within an area of the photoresist material layer 22'. It is further appreciated that four lasers 54 and four detectors 58 are shown, but any number of lasers and detectors can be employed to perform the present invention. It also is to be noted that a nozzle for applying the photoresist material is not shown, but the optimal location of the lasers 54 and detectors 58 can be very close to the surface of wafer 24', so that lasers 54 and the detectors 58 do not interfere with the nozzle.

The processor 40 receives the measured data from the measuring system 42 and determines the overall water particle count on the patterned photoresist material layer 22' by classical signal analysis and estimation algorithms. The processor 40 is programmed to control and operate the various components within the system 30 in order to carry out the various functions described herein. The processor or CPU 40 may be any of a plurality of processors, such as the AMD K7 and other similar and compatible processors. The manner in which the processor 40 can be programmed to carry out the functions relating to the present invention will be readily apparent to those having ordinary skill in the art based on the description provided herein.

A memory 34 which is operatively coupled to the processor 40 is also included in the system 30 and serves to store program code executed by the processor 40 for carrying out operating functions of the system 30 as described herein. The memory 34 includes read only memory (ROM) and random access memory (RAM). The ROM contains among other code the Basic Input-Output System (BIOS) which controls the basic hardware operations of the system 30. The RAM is the main memory into which the operating system and application programs are loaded. The memory 34 also serves as a storage medium for temporarily storing information such as water particle count measurements, water particle count coordinate tables, laser setting information, detector sensitivity information and other data which may be employed in carrying out the present invention. For mass data storage, the memory 34 may include a hard disk drive (e.g., 10 Gigabyte hard drive).

Power supply 32 provides operating power to the system 30. Any suitable power supply (e.g., battery, line power) may be employed to carry out the present invention. It is to be appreciated that any suitable laser scattering or laser doppler anemometry system may be employed to carry out the present invention and such systems are intended to fall within the scope of the hereto appended claims. Laser scattering and laser doppler anemometry systems are well known in the art, and therefore further discussion related thereto is omitted for sake of brevity.

Figure 2B:
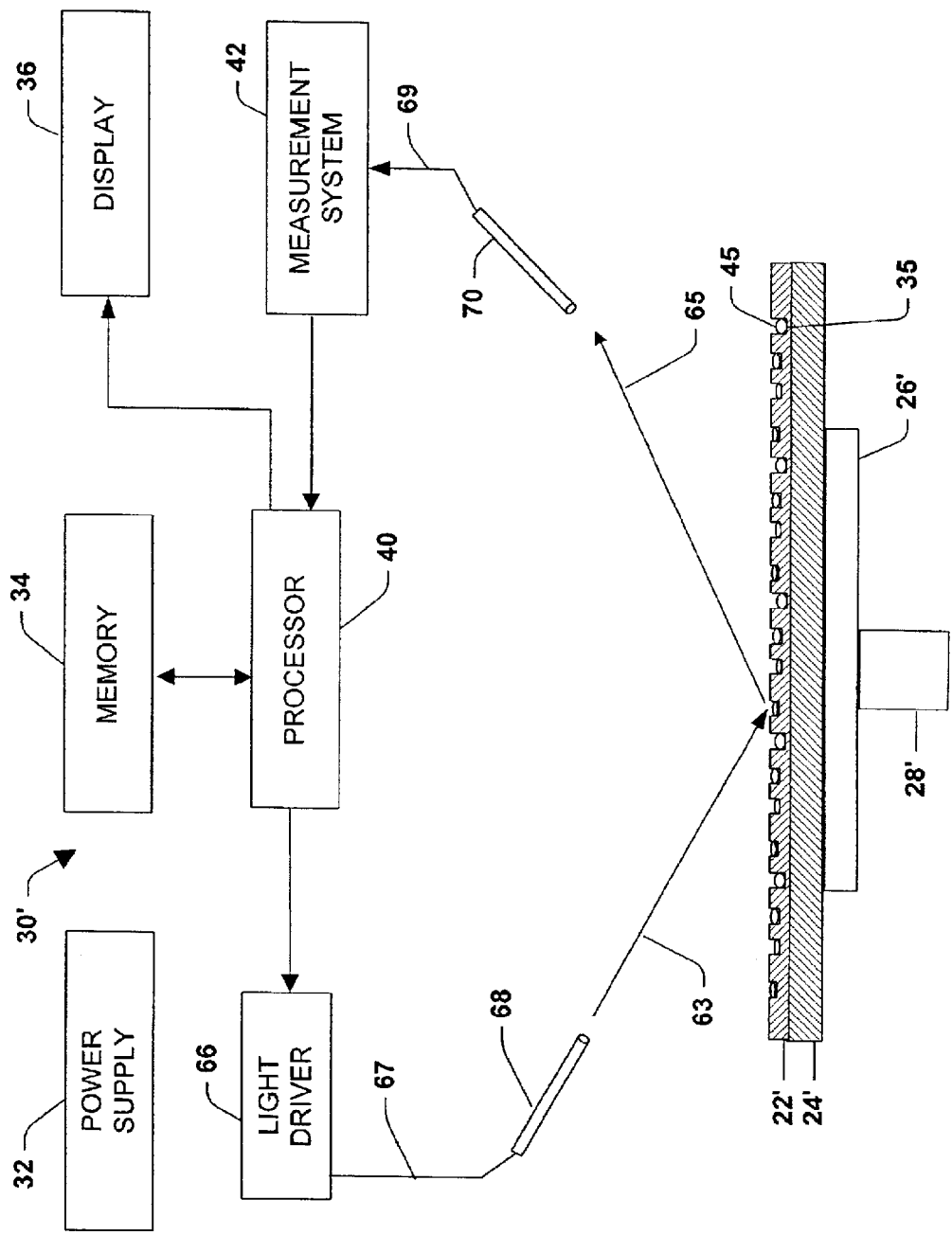
FIG. 2b is a representative schematic block diagram of an alternate monitoring system in accordance with one particular aspect of the present invention.

Alternatively, the measurement system 42 can employ polychromatic interferometer system or a monochromatic interferometer system to measure the water particle count. For example, FIG. 2*b* illustrates a monitoring system 30' for monitoring water particles formed from a development process similar to the monitoring system 30 illustrated in FIG. 2*a* were like parts are denoted by like reference numerals. However, the monitoring system 30' includes a light source 68 connected by a fiber optic line 67 to a light driver 66. The light driver 66 is turned on and off for water particle measurements on the patterned photoresist material layer 22' by the processor 40. The light source 68 sends a ray of light 63 at the resist layer 22', which is reflected as a ray of light 65 to a light receiver 70 coupled to the measurement system 42 for making water particle measurements. The light receiver 70 is connected to the measurement system 42 by a fiber optic line 69. In another aspect of the invention, the light source 68 and the light receiver 70 are rotatable so that water particle measurements can be performed at various points along the patterned photoresist material layer 22'. In yet another aspect of the invention, the light source 68 comprises a plurality of fiber optic connections and light sources and light receiver 70 includes a plurality of fiber optic connections, and light receivers for detecting water particles 45 along different vias 35 in the resist layer 22'.

Any suitable interferometry system and/or spectrometry system may be employed to carry out the present invention and such systems are intended to fall within the scope of the hereto appended claims. In one embodiment, the measurement system 42 is a polychromatic interferometer system or a monochromatic interferometer system to measure the water particles formed on the patterned photoresist material layer 22'. In another embodiment, the measurement system 42 is a spectrometry system. Interferometry systems and spectrometry systems are well known in the art, and therefore further discussion related thereto is omitted for sake of brevity. It is to be appreciated that the processor 40, power supply 32, memory 34 and display 36 may operate similarly in both the monitoring system 30' of FIG. 2*b* and the monitoring system 30 of FIG. 2*a*.

Figure 3:
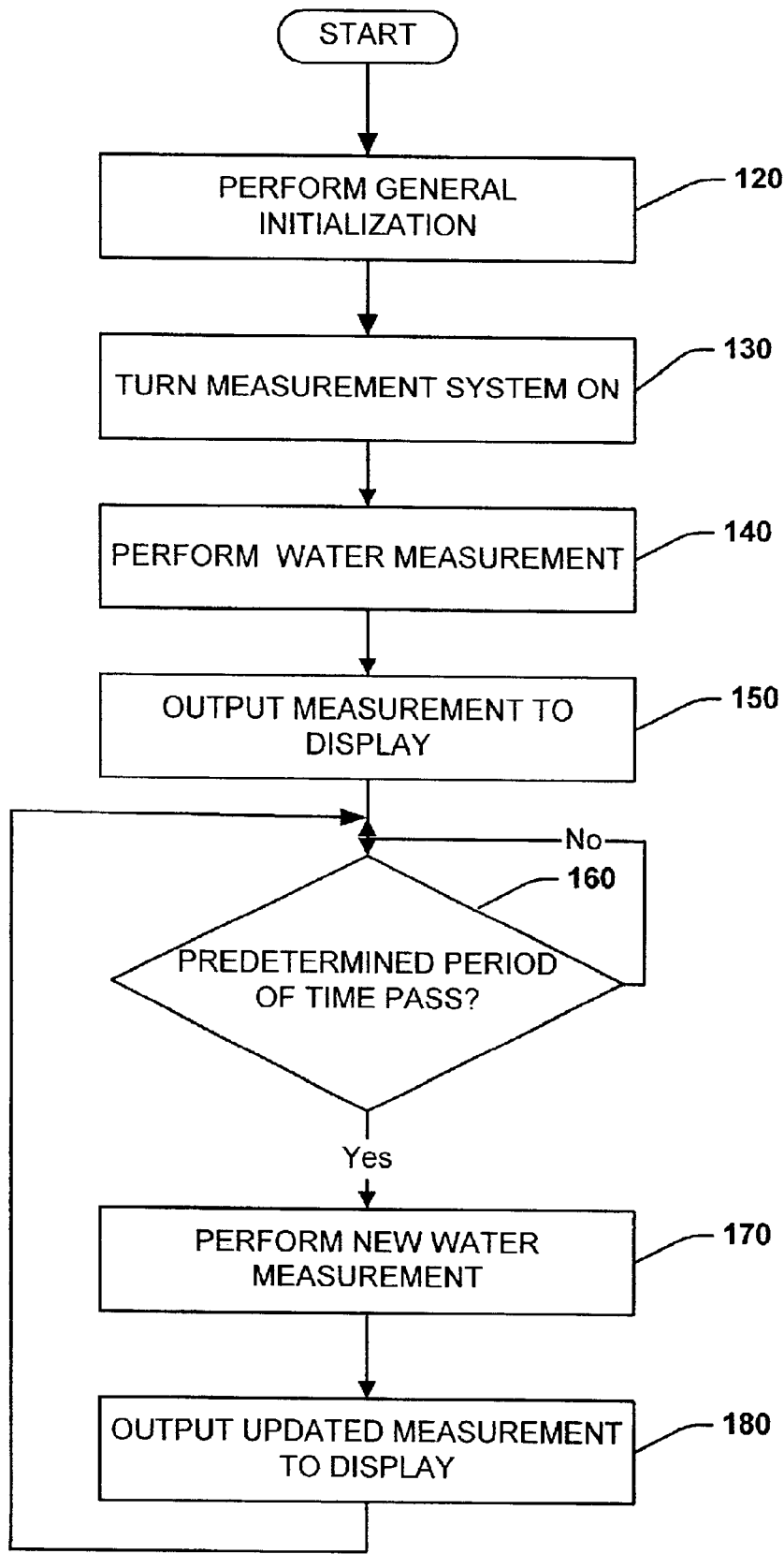
FIG. 3 is a flow diagram illustrating one specific methodology for carrying out the monitoring system of FIG. 2a in accordance with the present invention.

FIG. 3 illustrates one particular methodology for carrying out the monitoring system 30 of the present invention utilizing a multiple laser and detector arrangement as described in FIG. 2*a*. However, a light scattering and detector arrangement as described in FIG. 2*b* can be employed to carry out a similar methodology. In step 120, power is provided to the system 30 and the processor 40 performs general initializations to the water particle count monitoring system 30. In step 130, the processor 40 turns the laser driver 38 on causing lasers 54 to send beams of light 56 across the patterned photoresist material layer 22 to detectors 58. In step 140, the measurement system 42 performs a water particle count measurement and sends the data to the processor 40. In step 150, the processor 40 analyzed the measured data and outputs the data to the display 36. The processor 40 then determines if a predetermined period of time has passed in step 160. If no, the processor repeats step 160. If yes, the processor 40 advances to step 170 where a new water particle measurement is performed. In step 180, the processor 40 outputs the updated measurement to the display 36 and returns to step 160. The present methodology illustrates where the system 30 performs continuous monitoring and updates to the display, and can be disabled by powering down the monitoring system. It is be noted that the processor 40 can be programmed to perform monitoring at specific periods during the development process.

Figure 4:
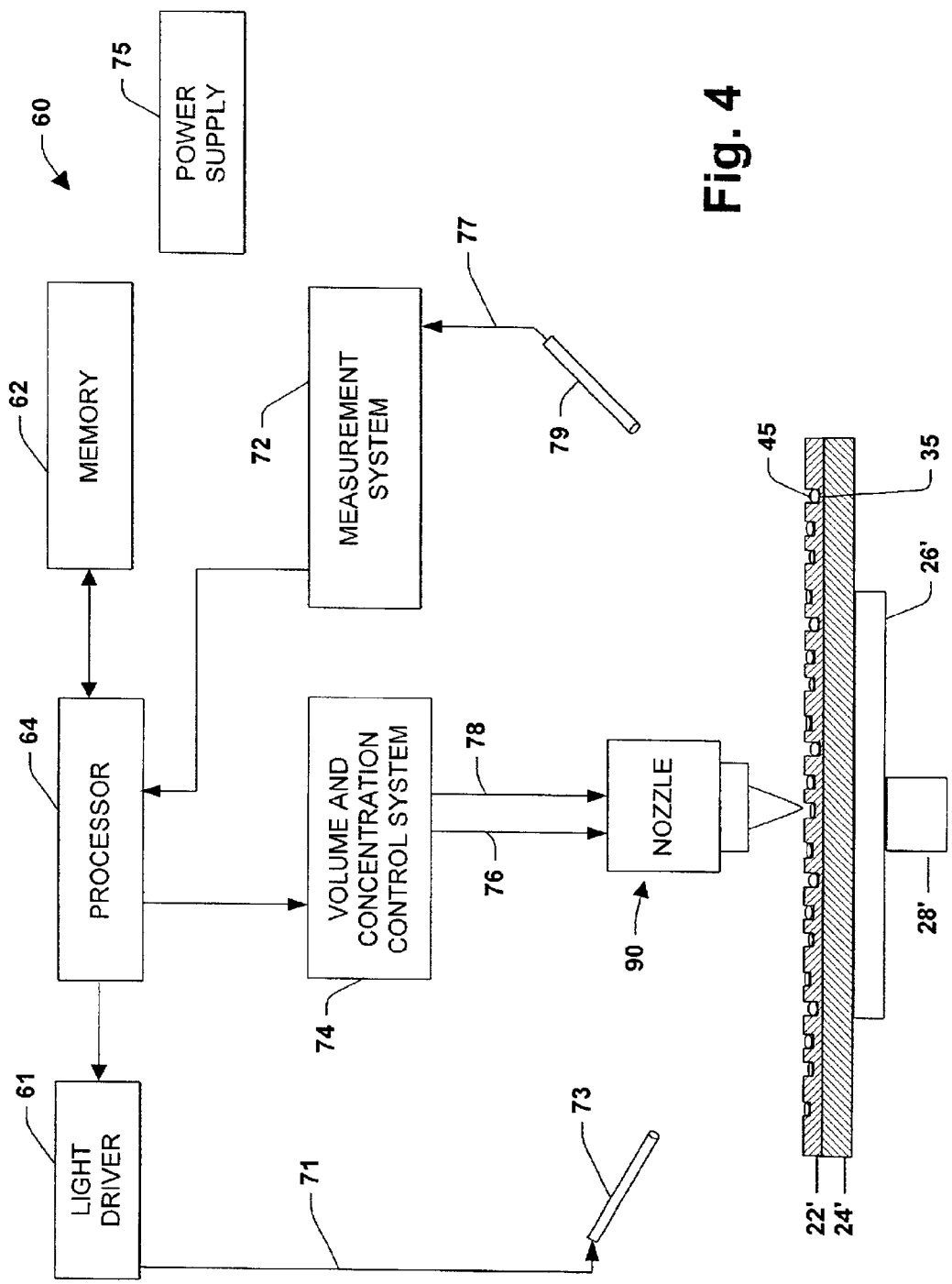
FIG. 4 is a representative schematic block diagram of a control system in accordance with one particular aspect of the present invention.

FIG. 4 illustrates a closed loop system 60 for controlling the developer concentration, the volume of developer applied and the development time when applying developer to the photoresist material layer 22' on the wafer 24' as shown. The system 60 includes a water particle measurement system 72. The system 60 includes a light source 73 connected by a fiber optic line 71 to a light driver 61. The light driver 61 is turned on and off for water particle measurements on the photoresist material layer 22' by the processor 64, after the development of a pattern onto the photoresist material layer 22'. The light source 73 sends light at the resist layer 22', which is reflected to a light receiver 79 coupled to the measurement system 72 for making water particle measurements. The light receiver 79 is connected to the measurement system 72 by a fiber optic line 77.

The processor 64 receives measured water particle data from the measuring system 72 and determines the overall acid consumption of the development process. A memory 62 which is operatively coupled to the processor 64 is also included in the system 60 and serves to store program code executed by the processor 64 for carrying out operating functions of the system 60. Power supply 75 provides operating power to the system 60. Any suitable power supply (e.g., battery, line power) may be employed to carry out the present invention.

The processor 64 is also coupled to a volume and concentration control system 74. The volume and concentration control system 74 is operatively coupled to a nozzle 90, which applies developer to the center of photoresist material 22'. It is to be appreciated although a single nozzle 90 is illustrated, the developer application system 20 can be employed that implements a plurality of similar nozzles.

The developer material is formed by a combination of concentrated developer and water added to the concentrated developer. The water combines with the concentrated developer to control the concentration of the developer, so that an optimized concentration level can be obtained. The total volume of the developer and the ratio of developer and water mixture is maintained by electronically controlled valves controlled by control line 76 and 78 of the volume and mixture control system 74. The volume and concentration control system 74 may also be programmed to control a developer contact time.

Figure 5A:
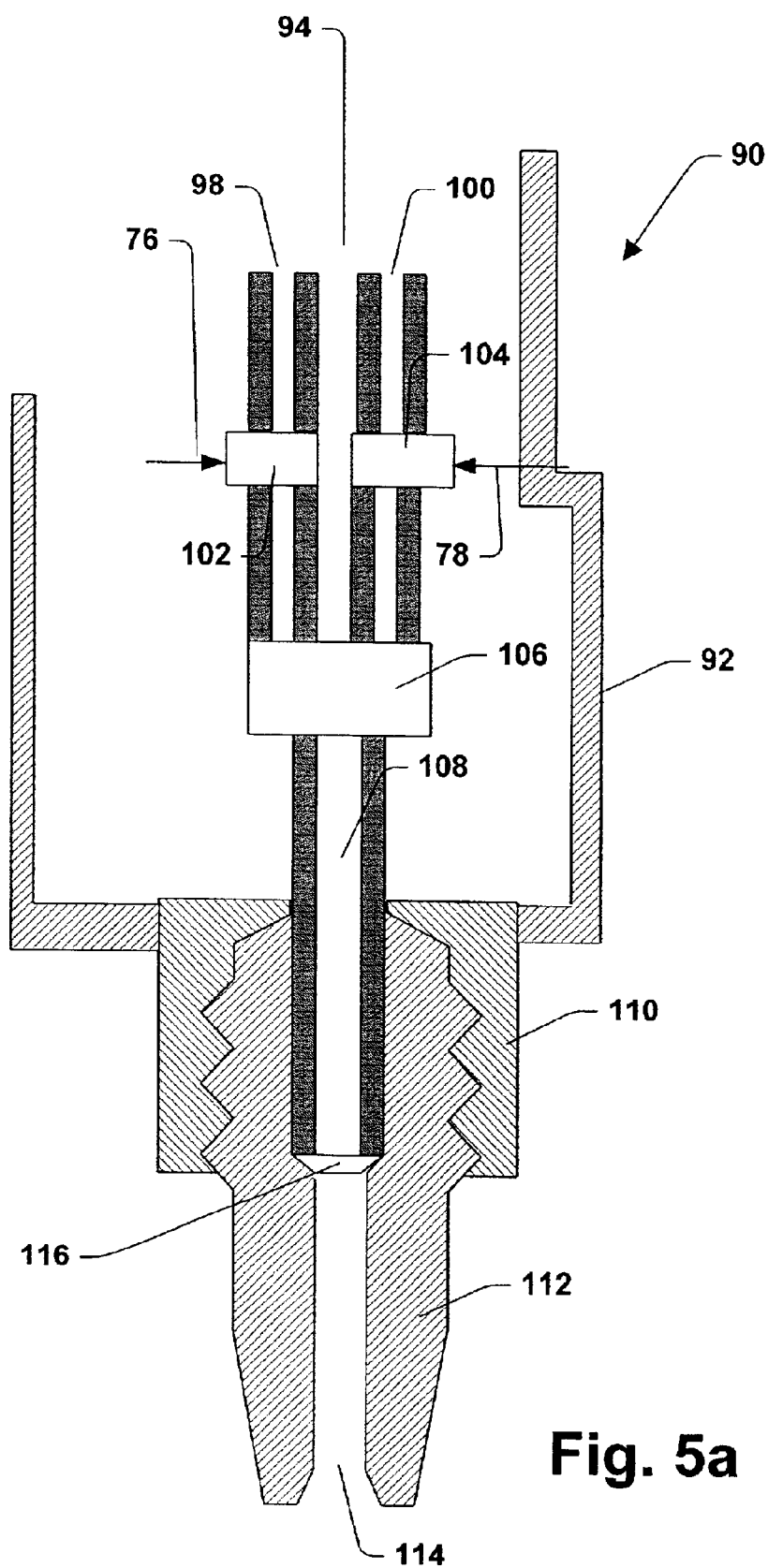
FIG. 5a illustrates a cross-sectional view of a nozzle in accordance with one particular aspect of the present invention.

Referring now to FIG. 5a, the nozzle 90 includes a holder 92 holding a concentrated developer supply tube 98 with one end disposed within the holder 92 and its other end connected to a supply of developer (not shown). A water supply tube 100 has one end disposed within the holder 92, and its other end connected to a supply of water (not shown). A concentrated developer adjustment valve 102 and a water adjustment valve 104 determine the amount of concentrated developer and water that is received into a mixing chamber 106. It is to be appreciated that a static mixer may be employed to facilitate mixing. Both valves are electronically controlled by control lines 76 and 78, respectively, coupled to the volume and concentration control system 74. The valves can determine the amount of concentrated developer and water that will be applied to the photoresist layer 22', after a pattern is irradiated onto the photoresist layer 22', and also the ratio of the concentrated developer and water in the concentrated developer and water mixture. The mixing of the concentrated developer and water is provided in the mixing chamber 106 simply by simultaneously supplying concentrated developer and water in the chamber. Other mixing techniques can be employed to provide mixing of the concentrated developer and water (e.g. vibration, rotation, churning etc.). A collar 110 is connected to the bottom of the holder 92 and includes a central aperture for allowing a concentrated developer and water mixture supply barrel 108 to pass therethrough. The collar 110 threadingly engages a nozzle tip 112. Supply barrel 108 is connected to the mixing chamber 106 on one end and passes through the center of nozzle tip 112 on its other end. The supply barrel 108 includes a liquid discharge opening 116 that discharges the concentrated developer and water mixture through a liquid discharge channel 114 of the nozzle tip 112 to the center of the photoresist material layer 22'.

Figure 5B:
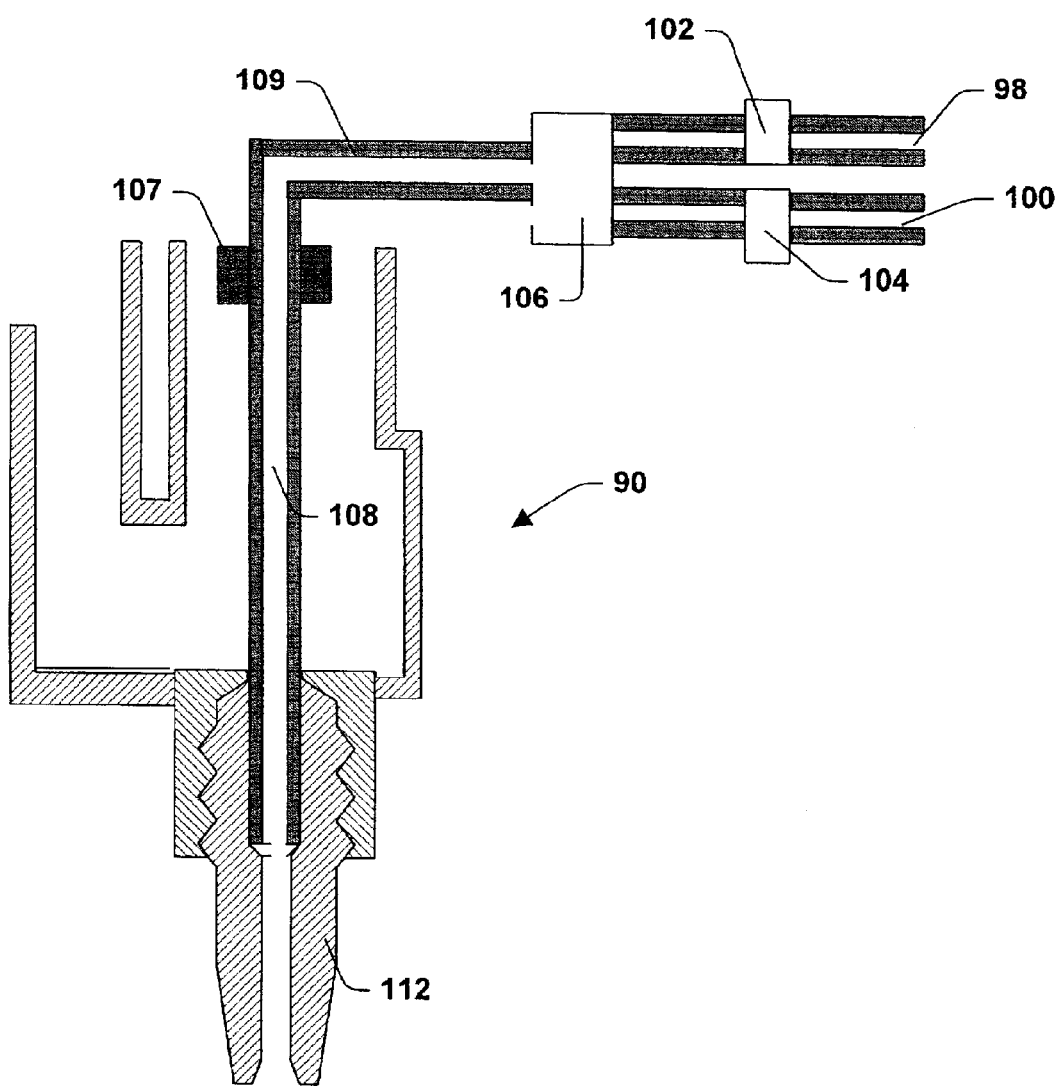
FIG. 5b illustrates a cross-sectional view of an alternate nozzle in accordance with one particular aspect of the present invention.

It is to be appreciated that the mixing of the concentrated developer and water can take place outside the nozzle 90. Such an example is illustrated in FIG. 5b, where the supply barrel 108 is disposed inside the nozzle 90 and is coupled to a developer supply line 109 by a coupler 107. The supply line 109 connects to the mixing chamber 106. The mixing chamber 106, the concentrated developer supply tube 98 and the water supply tube 100 are located outside the nozzle 90. Additionally, the concentrated developer adjustment valve 102 and the water adjustment valve 104 are also located outside the nozzle 90.

Figure 6:
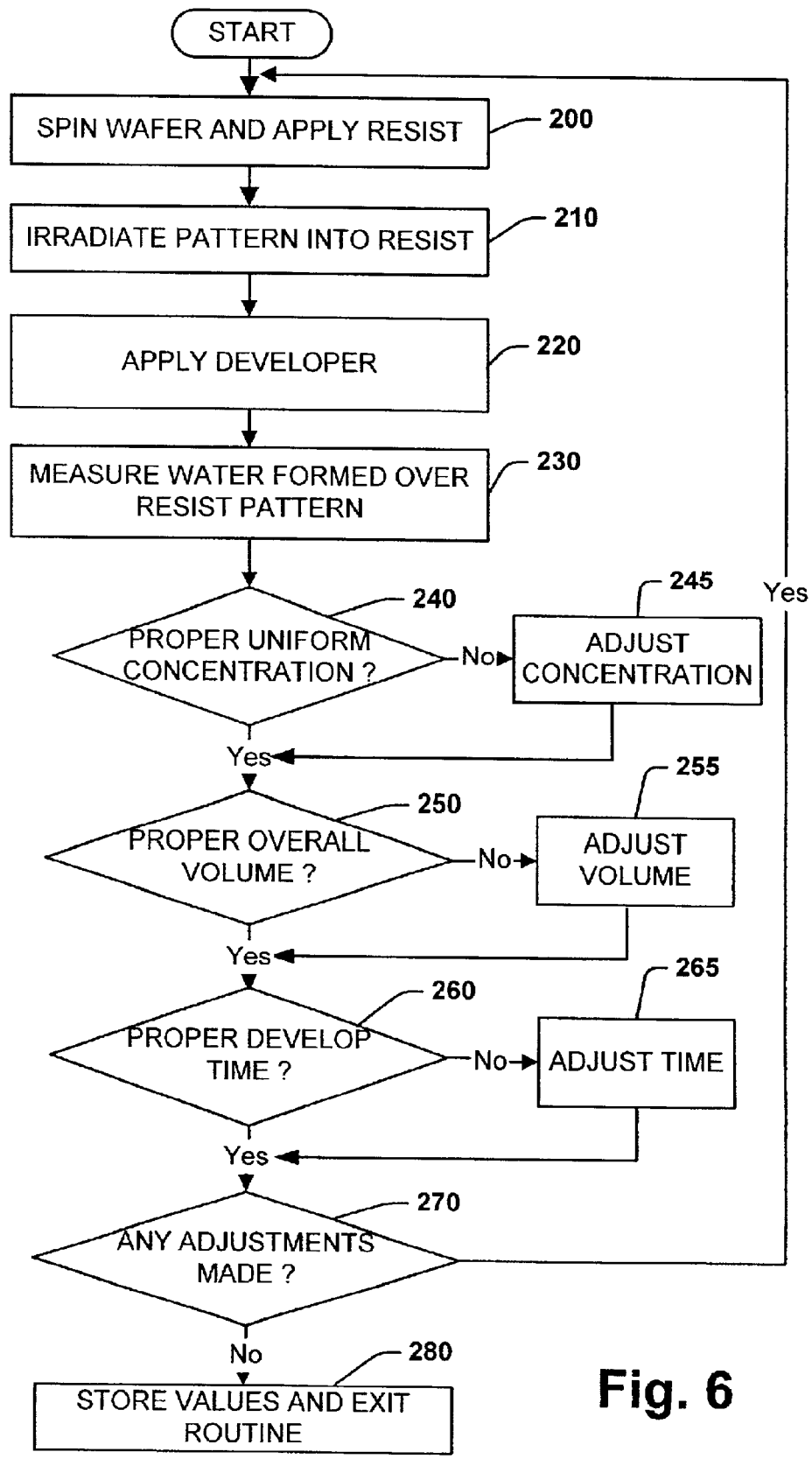
FIG. 6 is a flow diagram illustrating one specific methodology for carrying out the control system of FIG. 4 in accordance with the present invention.

FIG. 6 is a flow diagram illustrating one particular methodology for carrying out the present invention with respect to the control system 60 of FIG. 4. In step 200, a wafer 24' is loaded onto the rotating chuck 26' and a photoresist layer is spin coated onto the wafer 24'. In step 210, an image or pattern is irradiated onto the photoresist layer after the photoresist layer dries. In step 220, a predetermined ratio and volume of a concentrated developer and water mixture is applied to the photoresist layer, based on known characteristics of the photoresist material and the developer. The developer is then left on the wafer for a period of time until the photoresist layer is developed. The measurement system 72 then measures the amount of water particles on the patterned photoresist layer 22' at various locations along the wafer in step 230. In step 240, the processor 64 determines if the amount of water particles across the patterned photoresist layer 22' equates to the optimal acid consumption of the photoacid generator in the photoresist material based on the particular pattern, the particular desired chemical reaction ratio, the known concentration and amount of acid verse the applied concentration volume and concentration of the developer and the amount of development time. The processor 64 then determines if the proper uniform concentration developer concentration was applied. If the proper uniform concentration of developer was not applied (No), the processor 64 adjust the developer concentration in step 245 and advances to step 250. If the proper uniform concentration of developer was applied (Yes), the processor 64 simply advances to step 250. In step 250, the processor 64 then determines if the proper overall volume of developer was applied. If the proper overall volume of developer was not applied (No), the processor 64 adjust the volume of developer in step 255 and advances to step 260. If the proper overall volume of developer was applied (Yes), the processor 64 advances to step 260. In step 260, the processor 64 then determines if the proper development time was utilized. If the proper development time was not utilized (No), the processor 64 adjust the development time in step 265 and advances to step 270. If the proper development time was utilized (Yes), the processor 64 advances to step 270. In step 270, the processor 64 determines if any adjustments have been made. If any adjustment have been made (Yes), the processor returns to step 200 and repeats the procedure for another wafer, until the optimal developer concentration and volume and optimal development time has been achieved for that particular pattern. If adjustments have not been made (No), the processor 64 stores the variables into memory 62 in step 280 for use in mass production and exits the routine.

What has been described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system of monitoring development of a selectively irradiated photoresist material layer comprising:
    at least one light source disposed near the selectively irradiated photoresist material layer, the at least one light source adapted to transmit a ray of light across the selectively irradiated photoresist material layer;
    at least one detector disposed near the selectively irradiated photoresist material layer, the at least one detector adapted to receive a reflected ray of light due to the at least one light source and provide a signal corresponding to the intensity of the reflected ray of light;
    a measuring system operably coupled to the at least one detector, the measuring system adapted to receive the signal corresponding to the intensity of the ray of light and convert the signal to digital data, the measuring system measuring at least one of volume of developer, concentration of developer and period of contact time between developer and selectively irradiated photoresist; and a processor operatively coupled to the measuring system, the processor adapted to receive the digital data from the measuring system and analyze the digital data wherein the difference of the intensity of the ray of light from the at least one light source to when it is received by at least one detector is proportional to an amount of water generated across the selectively irradiated photoresist material layer due to an interaction of a developer and an acid in the selectively irradiated photoresist material layer.

2. The system of claim 1, wherein the measuring system applies in-situ laser scattering.

3. The system of claim 1, wherein the measuring system applies laser doppler anemometry.

4. The system of claim 1, wherein the measurement system applies interferometry.

5. The system of claim 1, wherein the measuring system applies spectrometry.

6. The system of claim 1, wherein the processor outputs the analyzed data to a display.

7. The system of claim 1, wherein the at least one light source includes a first light source directed at a first area of the selectively irradiated photoresist material layer and a second light source directed at a second area of the selectively irradiated photoresist material layer and the at least one detector includes a first detector disposed at a location adapted to receive reflected light from the selectively irradiated photoresist material layer due to the first light source and a second detector disposed at a location adapted to receive reflected light from the selectively irradiated photoresist material layer due to the second light source.

8. A system of controlling development of a selectively irradiated photoresist material layer comprising:

a nozzle adapted to contact the selectively irradiated photoresist material layer with a volume of developer having a concentration for a period of time;

a measuring system adapted to measure an amount of water generated on the selectively irradiated photoresist material layer due to an interaction of the developer and an acid in the selectively irradiated photoresist material layer, the measuring system further measuring at least one of volume of developer, concentration of developer and period of contact time between developer and selectively irradiated photoresist; and a processor operatively coupled to the measuring system and a developer volume and concentration control system, the processor receiving data from the measuring system relating to the amount of water measured and the processor using the data to determine acid consumption of the selectively irradiated photoresist material layer, the processor being further adapted to provide adjustment information to the developer volume and concentration control system for adjusting at least one of the volume of developer, the concentration of developer and the period of contact time, so that a subsequent selectively irradiated photoresist material layer having a more uniform development can be achieved.

9. The system of claim 8, wherein the measuring system is one of an in-situ laser scattering system, a laser doppler anemometry system, an interferometry system and a spectrometry system.

10. The system of claim 8, wherein the developer is a mixture of concentrated developer and water.

11. The system of claim 10, wherein the developer volume and concentration control system adjusts the concentration of the developer by varying an amount of concentrated developer and water in the mixture.

12. The system of claim 11, wherein an electronically controlled valve controls the flow of at least one of the concentrated developer and water that flows into a mixing chamber, wherein the concentrated developer and water mixture is formed.

13. The system of claim 12, wherein the electronically controlled valve and the mixing chamber are disposed inside the nozzle.

14. A system of developing a selectively irradiated photoresist material layer disposed on a semiconductor wafer comprising:

means for contacting the selectively irradiated photoresist material layer with a volume of developer having a concentration for a period of time whereby the developer and an acid in the photoresist material layer interact to generate an amount of water;

means for measuring the amount of water, the measuring means further measuring at least one of volume of developer, concentration of developer and period of contact time between developer and selectively irradiated photoresist; and means for determining an amount of acid consumption based on the amount of water measured.

15. The system of claim 14, further including means for adjusting the concentration of the developer based on the determined acid consumption.

16. The system of claim 14, further including means for adjusting the volume of developer based on the determined acid consumption.

17. The system of claim 14, further including means for adjusting the contact time.

18. The system of claim 15, further including means for controlling the means for applying a developer.

19. The system of claim 1, wherein the measuring system measures volume of developer contacted with the selectively irradiated photoresist.

20. The system of claim 1, wherein the measuring system measures concentration of developer.

21. The system of claim 1, wherein the measuring system measures period of contact time between developer and selectively irradiated photoresist.

22. The system of claim 8, wherein the measuring system measures volume of developer contacted with the selectively irradiated photoresist.

23. The system of claim 8, wherein the measuring system measures concentration of developer.

* * * * *